United States Patent [19]

Rohrschneider et al.

[11] Patent Number: 4,837,237

[45] Date of Patent: Jun. 6, 1989

[54] THERAPY USING GLUCOSIDASE PROCESSING INHIBITORS

[75] Inventors: Larry R. Rohrschneider, Mercer Island, Wash.; Everett J. Nichols, 1501 - 1st Ave. N., #3A, Seattle, Wash. 98109

[73] Assignees: Fred Hutchinson Cancer Research Center; Everett J. Nichols, both of Seattle, Wash.

[21] Appl. No.: 753,686

[22] Filed: Jul. 9, 1985

[51] Int. Cl.$^4$ ...................... A61K 31/70; G01N 33/48
[52] U.S. Cl. ......................................... 514/62; 514/23; 514/283; 514/345; 514/729; 514/738; 436/63; 436/64
[58] Field of Search .................. 424/85; 514/283, 345, 514/729, 738, 62, 23; 435/172.2, 200, 207, 208, 240.2; 436/63, 64

[56] References Cited

PUBLICATIONS

Pinter, A. et al., "Studies with Inhibitors of Oligosaccharide Processing Indicate a Functional Role for Complex Sugars in the Transport and Proteolysis of Friend Mink Cell Focus–Inducing Murine Leukemia Virus Envelope Proteins", Virology, vol. 136, pp. 196–210, 1984.

Pan, Y. T. et al., "Castanospermine Inhibits the Processing of the Oligosaccharide Portion of the Influenza Viral Hemagglutinin", Biochemistry, pp. 3975–3984, 1983.

Virology 132:95–109, 1984.

Molecular and Cellular Biology 4(10): 1999–2009, Oct. 1984.
Proc. Natl. Acad. Sci. U.S.A. 81: 85–89, Jan. 1984.
TIBS, pp. 32–33, Jan. 1984.
The EMBO Journal 4(1): 105–112, 1985.
Cell 40: 971–981, Apr. 1985.
Cell 39: 327–337, Dec. 1984 (Part 1).

Primary Examiner—Blondel Hazel
Attorney, Agent, or Firm—Christensen, O'Connor, Johnson & Kindness

[57] ABSTRACT

A method of regulating oncogene-mediated cell transformation in a mammalian host. Oncogenes having glycosylated expression products are regulated by administering an effective amount of a processing glucosidase inhibitor: a glucosidase I inhibitor, e.g., castanospermine, N-methyl-1-deoxynojirimycin, 1-deoxynojirimycin, 5-amino-5-deoxy-D-glucopyranose; or a glucosidase II inhibitor, e.g., bromoconduritol. The glucosidase I inhibitors are preferred, particularly castanospermine (CA) and N-methyl-1-deoxynojirimycin (MdN). Oncogenes having glycosylated expression products that are ultimately expressed on the plasma membrane or secreted from transformed cells are particularly susceptible to regulation by these anti-cancer drugs. Also provided is a method of regulating the immune system of a mammalian host. Administration of an effective amount of a processing glucosidase inhibitor suppresses proliferation and differentiation of monocytic and myeloblastic cells.

13 Claims, 14 Drawing Sheets

Fig. 6. Glycosylational Processing of the fms Gene Product

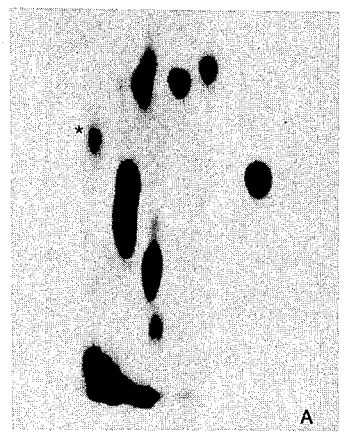
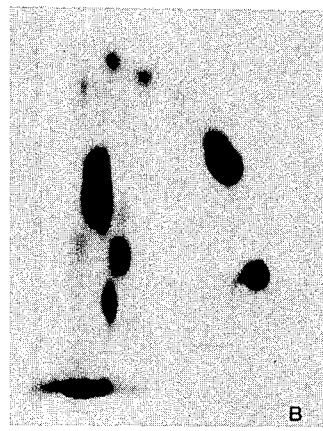
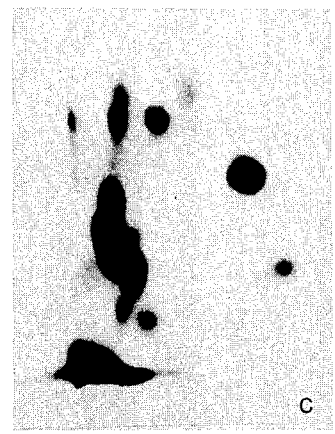
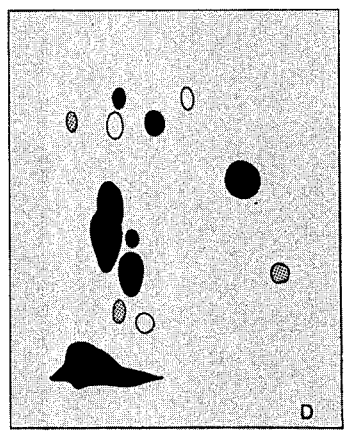
Fig. 12.

Fig. 14.

THERAPY USING GLUCOSIDASE PROCESSING INHIBITORS

This invention was made with Government support under Public Health Service Grants CA20551 and CA28151 from the National Cancer Institute. The Government has certain rights in this invention.

FIELD OF THE INVENTION

This invention relates to bio-affecting and body treating compositions, particularly to uses of processing glucosidase inhibitors for cancer chemotherapy and immunoregulation.

BACKGROUND OF THE INVENTION

Acute-transforming retroviruses carry in their genomes specific oncogenes that arose from recombination events between nontransforming viruses and normal cellular genes (proto-oncogenes or c-onc genes) that control growth and/or differentiation. In most of these retroviruses a single transforming protein is synthesized from the viral oncogene, and this protein product is responsible for initiation and maintenance of the transformed, cancerous state. About 30 acute-transforming retrovirus isolates have been reported so far, and these have been found to harbor about 20 distinct oncogenes. The fms, erbB, sis, and neu oncogenes are known to have glycosylated expression products, and the fms and erbB glycoproteins are ultimately expressed in the plasma membrane. In general, the insertion of the cellular gene within the viral genetic framework resulted in two critical alterations that permit a normal cellular gene to function in an uncontrolled manner within infected cells. First, the virus has provided a strong promoter for the cellular gene, enabling the overproduction of the acquired cellular gene, and second, in almost all cases the acquired cellular gene has been modified either through truncation or mutation. These quantitative and qualitative changes are believed to be important in neoplastic transformation by acute-transforming retroviruses and offer clues to the mechanism of transformation in the various viral oncogenes. It is therefore important to understand differences and similarities between the various v-onc and c-onc gene products.

In the specific case of the McDonough strain of feline sarcoma virus (SM-FeSV), the viral oncogene is called v-fms. This defective transforming virus was probably derived from a nondefective feline leukemia virus through in-frame insertion and replacement of part of the viral gag and all of the polymerase gene with an oncogene termed v-fms. The primary translation product of the v-fms oncogene is therefore a fusion protein of 160 kd initiating in gag and terminating at the end of v-fms ($P160^{gag-fms}$). Signal sequences at the start of gag direct the protein to the endoplasmic reticulum (ER) where carbohydrate is added to asparagine residues to give $gP180^{gag-fms}$, and cleavage of the gag sequences yields $gp120^{fms}$ plus $p55^{gag}$. A hydrophobic stretch of amino acids about midway through the sequence insures a transmembrane orientation with the C-terminal end of the fms proteins in the cytoplasm. Further processing in the Golgi results in a $gp140^{fms}$ species that ultimately is expressed on the plasma membrane. The $gp140^{fms}$ is associated with coated pits on the cell surface, is processed through endocytosis, and may function as a modified growth factor receptor on the surface of SM-FeSV-transformed cells.

The physical properties, cellular location, and fact that $gp140^{v-fms}$ undergoes endocytosis through coated pits and vesicles all point to a functional analogy with growth factor receptors. The $gp140^{v-fms}$ also exhibits an associated tyrosine kinase activity as do many growth factor receptors. Furthermore, the amino acid sequences of v-fms and acknowledge tyrosine kinases such as $pp60^{v-src}$ are homologous.

It would be advantageous to discover ways to intervene in the cellular expression of acute-transforming retroviruses and thereby cause transformed cells to revert to the normal phenotype (cancer remission). It would also be advantageous to discover the normal cellular counterparts of transforming oncogenes, so that the growth and/or differentiation of cells that express c-onc genes, either normally or abnormally, could be likewise modulated for therapeutic effect.

SUMMARY OF THE INVENTION

This invention provides a method of regulating oncogene-mediated cell transformation in a mammalian host. Oncogenes having glycosylated expression products are regulated by administering an effective amount of a processing glucosidase inhibitor: a glucosidase I inhibitor, e.g., castanospermine, N-methyl-1-deoxynojirimycin, 1-deoxynojirimycin, 5-amino-5-deoxy-D-glucopyranose; or a glucosidase II inhibitor, e.g., bromoconduritol. The glucosidase I inhibitors are preferred, particularly castanospermine (CA) and N-methyl-1-deoxynojirimycin (MdN). Oncogenes having glycosylated expression products that are ultimately expressed on the plasma membrane or secreted from transformed cells are particularly susceptible to regulation by these anti-cancer drugs.

Also provided is a method of regulating the immune system of a mammalian host. Administration of an effective amount of a processing glucosidase inhibitor suppresses proliferation and differentiation of monocytic and myeloblastic cells.

BRIEF DESCRIPTION OF THE DRAWINGS

FIG. 12 shows three two-dimensional tryptic fingerprints (A-C) and a summarizing schematic (D) demonstrating that BCP140 is structurally related to v-fms gp120$^{fms}$, as described in Example 13;

FIG. 14 shows two series of electrophoresis gels (A, 1-6, & B, 1-4) demonstrating that a protein which is antigenically related to BCP140 is (A) expressed in ML-1 cells induced to differentiate into monocytes, and (B) has an associated tyrosine kinase activity, both as descibed in Example 14.

DESCRIPTION OF THE PREFERRED EMBODIMENT

Figure 1:
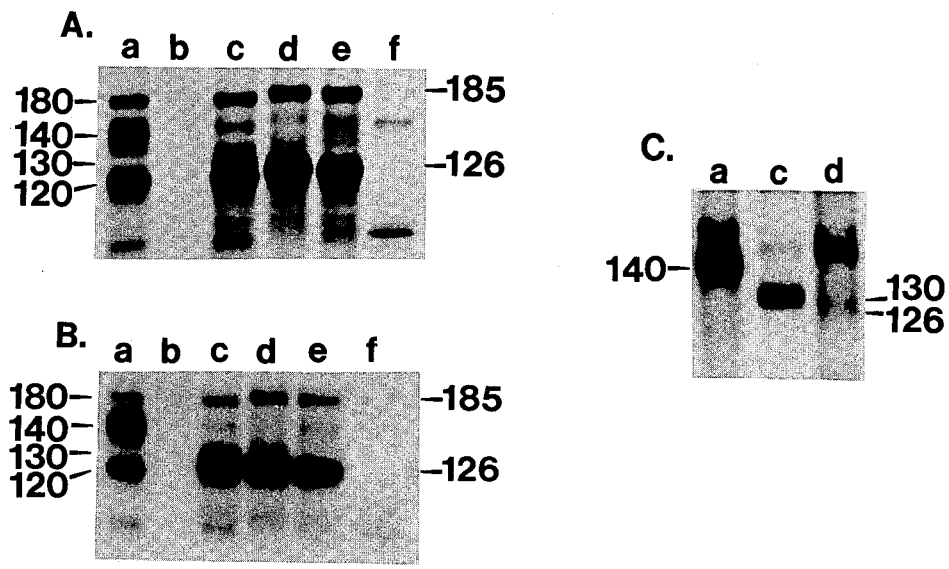
FIG. 1 shows three electrophoresis gels (A-C) that demonstrate the influence of carbohydrate processing inhibitors on metabolism (A), kinase activity (B), and cell surface expression (C) of the v-fms proteins; SM-FeSV-transformed Fischer rat embryo fibroblasts were grown in the absence (lanes a) or presence of either swainsonine (c), castanospermine (d), N-methyl-1-deoxynojirimycin (e), or tunicamycin (f), as described in Examples 1, 2, and 3.

Pursuant to this invention the cellular expression of acute-transforming retroviruses having glycosylated expression products is interrupted by the administration of processing glycosidase inhibitors, leading to remission of transformed cells to the normal phenotype. In particular, administration of the glucosidase I inhibitors castanospermine (CA) and N-methyl-1-deoxynojirimycin (MdN) interrupts the glycosylational processing and plasma membrane expression of the v-fms transforming glycoprotein, leading to cancer remission. These and similar processing glucosidase inhibitors should be effective in controlling cancers that are mediated by oncogenes with glycosylated products, e.g., neu and sis, particularly those oncogenes whose glycosylated products are expressed as putative growth factor receptors on the plasma membrane of transformed cells, e.g., erbB, or whose glycosylated products are secreted as putative growth factors from transformed cells.

These inhibitors are also effective in suppressing the proliferation of cells that normally express glycoprotein growth factor receptors on their surfaces. In particular, CA inhibits the proliferation of monocytes and macrophages that bear glycosylated c-fms expression products on their plasma membranes, thereby affording a measure of selective immunosuppression for therapeutic effect.

The following Examples are presented to illustrate the advantages of the present invention and to assist one of ordinary skill in making and using the same. The following Examples are not intended in any way to otherwise limit the scope of the disclosure or the protection granted by Letters Patent hereon.

FIRST SERIES OF EXAMPLES

Carbohydrate remodeling was discovered to be important for the expression of the v-fms proteins. Glycosylational processing inhibitors were found that, while having no effect on the associated tyrosine kinase activity of the v-fms proteins, prevented cell surface expression and caused v-fms transformed cells to revert to the normal phenotype. These inhibitors may be useful anticancer drugs.

To determine if glycosylational processing is necessary for the cell surface expression of the oncogene v-fms, we used inhibitors which prevent glycosylation or interfere with the glycosylational processing reactions occurring on the oligosaccharides following their attachment to the protein. These inhibitors include swainsonine (SW), castanospermine (CA), N-methyl-1-deoxynojirimycin (MdN), and tunicamycin (TU). Both CA and MdN inhibit the same processing enzyme, glucosidase I, resulting in glycoproteins with oligosaccharides containing 1-3 glucose residues and 7-9 mannose residues. SW, on the other hand, inhibits Golgi mannosidase II, resulting in glycoproteins accumulating hybrid-type oligosaccharides with one branch containing a high mannose structure and the other a complex-type structure. The action of the nucleoside antibiotic TU, which inhibits the formation of dolicho(Dol)-P-P-N-acetylglucosamine results in the complete blockage of oligosaccharide chain addition to potential N-linked sites. We report here the effects of glycosylation on cell surface expression and the resulting consequences in growth regulation.

EXAMPLE 1

Metabolic processing and kinase activity

The effects of the various glycosylational processing inhibitors on the synthesis and expression of the v-fms proteins were examined in SM-FeSV transformed Fischer rate embryo (SM-FRE) cells.

SM-FeSV-transformed Fischer rat embryo fibroblasts (Oncogene Science, Inc.) were incubated overnight in Dulbecco's Modified Eagle's Medium (DME) containing 5% fetal bovine serum (FBS) and the repsective inhibitor: SW, 58 μm; CA (Cal Biochem), 0.13 mM; MdN (from A. Herscovies, McGill University), 2 mM; or TU (Cal Biochem), 0.12 μM. The media were then replaced with methionine-free DME containing 5% dialysed FBS and the cells were labeled for four hours with L-[$^{35}$S]methionine in the absence or presence of the respective inhibitor. Cells were finally washed three times in ice cold PBS, RIPA detergent extracts prepared, and fms proteins detected by immune precipitation using 5 ul rat polyclonal anti-fms serum as described in Cell 39: 327-337, 1984. Immune complexes were washed four times in RIPA buffer, once in lysis buffer (100 mM NaCl, 10 mM Tris-HCl, pH 7.4, 0.5% NP-40) and analyzed on SDS-polyacrylamide gels.

Immunoprecipitation of extracts of [$^{35}$S]methionine labeled fibroblasts using antisera to v-fms encoded determinants demonstrate the normal complement of v-fms gene proteins (gP180$^{gag\text{-}fms}$, gp140$^{fms}$, and gp120$^{fms}$) in untreated control cells (FIG. 1A, lane a). When the SM-FRE cells were grown in the presence of the mannosidase II inhibitor, SW, synthesis of the gp140$^{fms}$ protein was prevented and a gp130$^{fms}$ species was found instead (FIG. 1A, lane c). Inhibition of glucosidase I in SM-FRE transformed cells with either CA or MdN resulted in an accumulation of v-fms proteins gP185$^{gag\text{-}fms}$ and gp126$^{fms}$ (FIG. 1A, lanes d and e). Pulse chase analysis following removal of CA and MdN showed that the gP180$^{gag\text{-}fms}$ and gp120$^{fms}$ were derived from the gP185$^{gag\text{-}fms}$ and gp126$^{fms}$ species (data not shown). The 5 kd decrease in mass of these proteins was probably due to removal of terminal glucose residues and perhaps some subsequent trimming of exposed mannose residues as has been reported for other glycoproteins synthesized in the presence of these same inhibitors. *J.Biol.Chem.* 259: 10129–10135, 1984; *EMBO J.* 2: 823–832, 1983; *Nature* 307: 755–758, 1984; *Virology* 132: 95–109, 1984. TU treatment of SM-FRE cells resulted in the synthesis of unglycosylated proteins P160$^{gag\text{-}fms}$ and p95$^{fms}$ (FIG. 1A, lane f) as reported previously. *J.Virol.* 44: 696–702, 1982.

The v-fms proteins that were produced in the presence of the various inhibitors contained altered carbohydrate moieties yet the associated in vitro tyrosine kinase activity of these proteins was largely unaltered. Immunoprecipitates prepared from unlabeled cells treated as described above were resuspended on 25 ul of kinase buffer (20 mM Tris-HCl, pH 7.5, 10 mM MgCl$_2$). Then gamma[$^{32}$P]ATP was added and incubated for ten minutes at room temperature. The reaction was stopped by addition of 10 mM EDTA, washed 3× in lysis buffer and analyzed by SDS-polyacrylamide gel electrophoresis. The results in FIG. 1B show that all processing intermediates produced in the presence of either SW, CA, or MdN contained a tyrosine kinase activity that phosphorylated the respective v-fms proteins in vitro. The unglycosylated proteins made in the presence of TU also contained this activity even though not as much protein was detectable (lane f).

EXAMPLE 2

Cell surface expression

The expression of the v-fms proteins on the surface of SM-FRE cells grown in the presence of the glycosylational processing inhibitors was assessed by both cell surface iodination and viable cell fluorescence studies.

Cells were incubated with the respective inhibitor for 48 hours and surface labeled with [$^{125}$I]iodine using chloramine T as described in *Cell* 39: 327–337, 1984, hereby incorporated by reference. Cell extracts were assayed for protein by the fluorescamine assay described in *Science* 128: 871–872, 1972, and normalized prior to immune precipitation. Iodinated fms-proteins were analyzed on an SDS polyacrylamide gel. Molecular weight markers were coelectrophoresed. The results in FIG. 1C demonstrate the cell surface iodination experiments. Normally, only the gp140$^{fms}$ species is detectable on the surface of SM-FeSV transformed cells, (lane a). When SW is included in the growth medium, gp140$^{fms}$ is not detectable on these cells (in agreement with the results shown in FIG. 1A) but the new species, gp130$^{fms}$, is expressed on the cell surface (FIG. 1C, lane c). The iodinated protein bands in the 150–160 kd range in panel c are nonspecific background. Very little if any of the v-fms proteins were found on the cell surface of CA (lane d) or MdN (not shown) treated cells.

Figure 2:
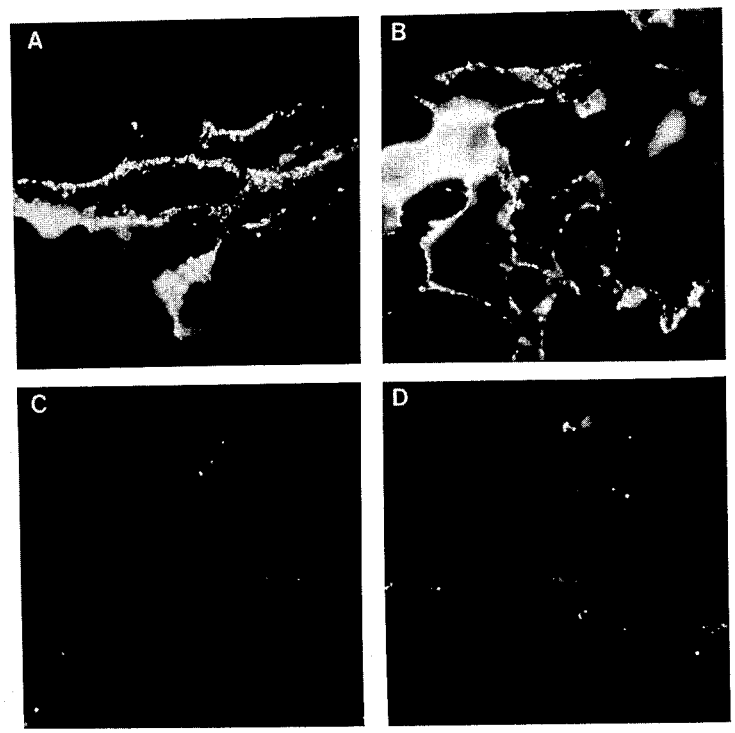
FIG. 2 shows four micrographs (A-D) demonstrating the cell surface expression and distribution of v-fms proteins as determined by viable cell immunofluorescence; SM-FeSV transformed FRE cells were untreated (A), or treated with SW (B), CA (C), or MdN (D), as described in Example 2.

The expression and distribution of v-fms proteins on the surface of SM-FRE cells as examined by viable cell immunofluorescence using anti-fms sera is shown in FIG. 2. SM-FRE cells were plated onto glass coverslips in the bottom of 24 well plates and grown for 24 hours in either normal growth medium (A), or growth medium containing 58 μM SW (B), 0.13 mM CA (C), or 2 mM MdN (D). The expression of fms-specific determinants on the surface of the live SM-FRE cells was analyzed using rat anti-fms serum, exactly as described in *Cell* 39: 327–337, 1984.

As we have shown previously (*Cell* 39: 327–337, 1984), untreated SM-FeSV transformed FRE cells exhibited a punctate distribution of gp140$^{fms}$ on the cell surface (FIG. 2A). This pattern is due, in part, to the association of gp140$^{fms}$ with coated pits. SM-FRE cells grown in the presence of SW (FIG. 2B) exhibited a similar distribution and intensity of fluorescence as that seen in the untreated control cells. Both the metabolic labeling and the cell surface iodination experiments indicated that in the presence of SW a gp130$^{fms}$ species was formed instead of the gp140$^{fms}$, and that the gp130$^{fms}$ is expressed on the cell surface. This expression is qualitatively and quantitatively similar to that seen in untreated control SM-FRE cells.

In contrast to cells grown in the presence of SW, both CA- and MdN-treated SM-FRE cells exhibited a greatly reduced level of cell surface fluorescence (FIGS. 2C and 2D). This weak cell surface fluorescence was diffuse and not punctate as on the control or SW-treated SM-FRE cells. In the presence of CA or MdN, only a gP185$^{gag\text{-}fms}$ and gp126$^{fms}$ species were detectable. The results of both the cell surface iodination and immunofluorescence experiments indicated that neither of these fms proteins was expressed on the cell surface.

TU treatment (0.12 mM) of SM-FRE cells completely prevented the expression of any fms-related proteins at the cell surface (data not shown).

EXAMPLE 3

Endocytosis

Our previous studies demonstrated that the cell surface gp140$^{fms}$ was to a large extent associated with clathrin-coated pits, and that the cell surface expressed fms protein was rapidly taken into the cell through endocytosis. *Cell* 39: 327–337, 1984. Here we report the effects of the glycosylation processing inhibitors on endocytosis of cell surface expressed fms proteins. SM-FRE cells were incubated with SW, CA, or MdN at the same concentrations used for immunofluorescence microscopy, and the cellular uptake of fms proteins into endocytotic vesicles was determined by immunoperoxidase electron mocroscopy as described in *Cell* 39: 327–337, 1984. SM-FRE cells, either untreated (A), or treated with SW (B), CA (C), or MdN (D), were reacted with anti-fms serum on ice. Following application of immune reagents for peroxidase staining, the cells were warmed to 37° C. for ten minutes, fixed, permeabilized, and incubated with diaminobenzidine. Thin sections, not counterstained with either uranyl acetate or lead citrate, were viewed and photographed in the electron microscope.

Figure 3:
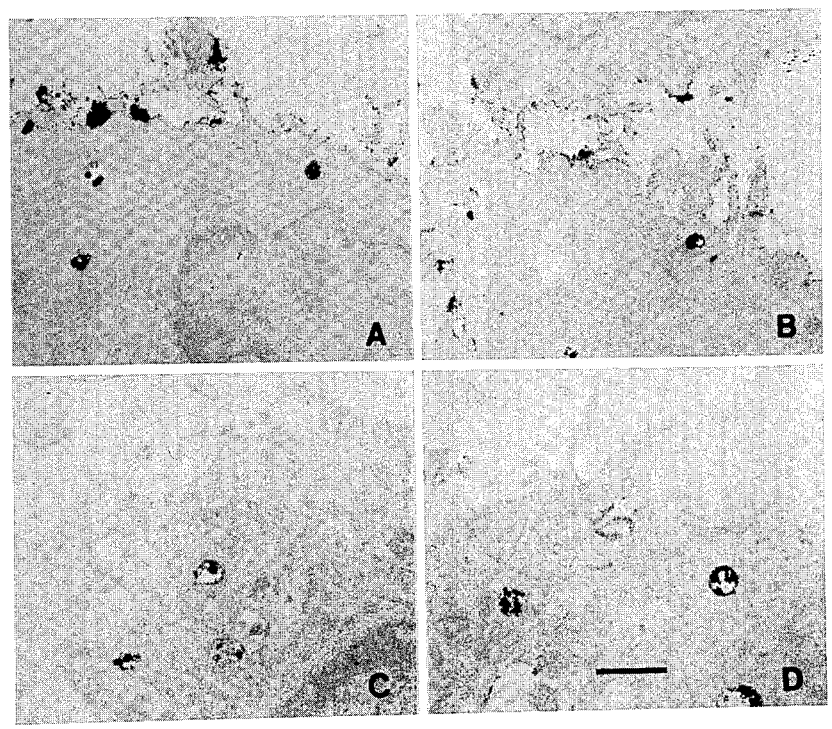
FIG. 3 shows four micrographs (A-D) demonstrating endocytosis of v-fms proteins in the absence (A) or presence of the carbohydrate processing inhibitors SW (B), CA (C), or MdN (D), as described in Example 3; the reference bar=1 μm.

Sections of peroxidase-stained SM-FRE cells viewed in the electron microscope displayed stainable perozidase reaction product within cytoplasmic vesicles regardless of the inhibitor treatment used. See FIG. 3: untreated (A), or treated with SW (B), CA (C), or MdN (D). However, the number of these positive vesicles per cell was dependent on the inhibitor treatment. To quantitate this effect for each treatment, cross-sections of fifty cells were viewed at random and the number of stained vesicles per cell determined. The glucosidase I inhibitors (CA and MdN) had the greatest effect, reducing the number of positive vesicles to 2.8±2.6 (arithmetic mean±s.d.) in MdN-treated cells and to 4.9±3.5 in CA-treated cells. This was in comparison to the number of positive vesicles in untreated control SM-FRE cells at 10.3±4.9. SW-treated cells, at 8.9±4.1, exhibited nearly the same number of positive vesicles as controls. Analysis of variance revealed that the reduction in the number of positive vesicles with either CA or MdN inhibitor was highly significant.

The decreased number of peroxidase positive endocytotic vesicles in the CA- and MdN-treated cells was probably due to the small amount of v-fms protein reaching the cell surface even in the presence of the inhibitors. This small amount was cleared completely from the cell surface within 10 min. (FIGS. 3C and 3D), whereas cell surface v-fms protein was still evident on the surface of both control and SW-treated cells after the same 10 min. incubation (FIGS. 3A and 3B).

EXAMPLE 4

Growth in soft agar

If the expression of the v-fms protein product gp140$^{fms}$ at the cell surface is important for oncogenic transformation, then two of the carbohydrate processing inhibitors (CA and MdN) may also modulate the transformed state of SM-FeSV transformed cells. We tested this possibility by determining the anchorage dependence of growth (soft agar colony assay) with SM-FRE cells grown in the presence and absence of the inhibitors.

Figure 4:
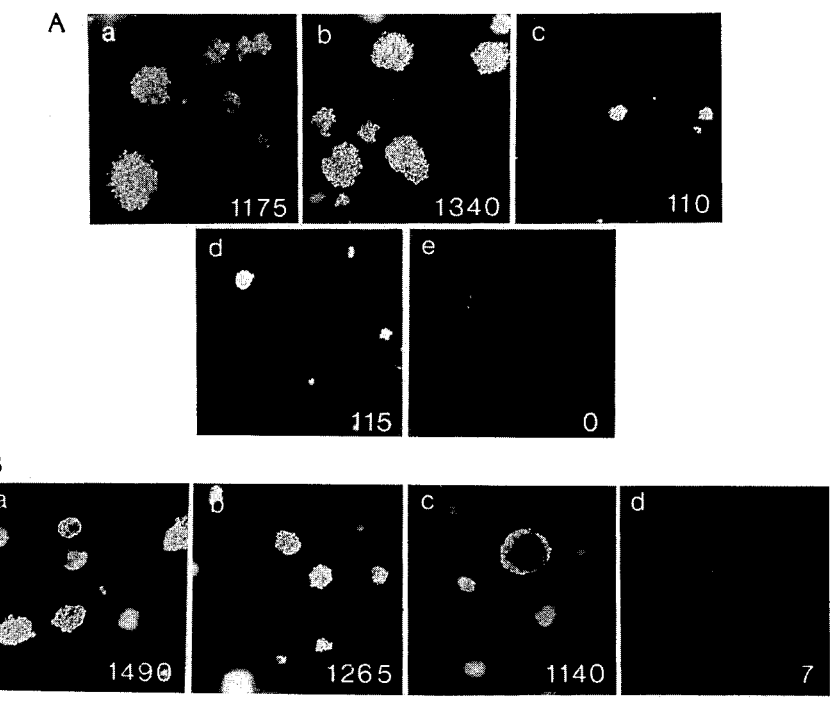
FIG. 4 shows nine micrographs (A, a-e, & B, a-d) demonstrating anchorage independent growth measured in the presence or absence of carbohydrate processing inhibitors, as described in Example 4.

Soft agar colony assays were performed, as described in *Experiments with Normal and Transformed Cells*, Cold Spring Harbor Lab., pp. 18–27, 1978, in 24 well plates (Costar). Referring to FIG. 4A, $2 \times 10^3$ SM-FRE cells were suspended in 1 ml 0.36% agar above a 0.6% agar bottom layer. Control wells contained no additions (a), whereas SW-treated (b), CA-treated (c), MdN-treated (d), and TU-treated (e) cells contained the inhibitors in both agar layers at 58 μM, 0.13 mM, 2 mM, and 0.12 uM, respectively. Eight days after seeding, the total number of colonies (>10 cells) in duplicate wells were counted with the aid of a grid and the average values are shown in each panel. The range between duplicates never exceeded 20% of the average value.

Referring to FIG. 4B, $2 \times 10^3$ Gardner-Rasheed FeSV-transformed FRE cells (Source: B. Sefton, Salk Institute, LaJolla, CA) were grown in agar suspension as described above in the absence (a) or presence (b) of 0.13 mM CA. In the same experiment, $2 \times 10^3$ SM-FRE cells were grown in the absence (c) or presence (d) of 0.13 mM CA. The total number of colonies (>10 cells) were counted in duplicate wells and the average values are presented in each panel.

SM-FRE cells in the absence of any inhibitor formed macroscopic colonies with about 60% efficiency. In The presence of SW, no decrease in colony size or number was noticed; in fact, in two separate experiments SW treatment resulted in a slightly higher efficiency of colony formation. In contrast to SW, growth of SM-FRE cells in the presence of either CA or MdN decreased 10-fold the ability of these cells to form colonies in soft agar. Even the colonies that did form in the presence of CA or MdN were much smaller than those that formed in the untreated control wells. It was also clear that neither CA nor MdN was toxic, since the treated cells appeared viable and could be picked from the agar and regrown in culture. TU treatment was toxic, however, and no colonies formed in the presence of this inhibitor due to cell death.

We considered the possibility that the reversal of anchorage independence of growth caused by CA and MdN in SM-FRE cells could have been due to the indirect action of these inhibitors on a cellular glycoprotein rather than directly on the v-fms glycoproteins. This notion was tested by comparing the effect of CA on the ability of Gardner-Rasheed FeSV-transformed FRE (GR-FRE) cells and the SM-FRE cells to form colonies in soft agar. The Gardner-Rasheed strain of FeSV carries the v-fgr oncogene (*Science* 223: 63–66, 1983) whose protein product is associated with a tyrosine kinase activity (*Virology* 125: 502–507, 1983) but is not expressed on the cell surface and is not glycosylated (unpublished observation). CA had no significant effect on the formation of soft agar colonies by the GR-FRE cells, whereas in this experiment CA caused a 100-fold reduction in the number of SM-FRE colonies. These results indicate that the actions of the drugs are specific for SM-FeSV transformed cells as compared with GR-FRE cells. Both CA and MdN return SM-FRE cells to more anchorage dependent growth, and this effect is most likely due to the prevention of cell surface expression of the v-fms gene product.

EXAMPLE 5

Cell morphology

Figure 5:
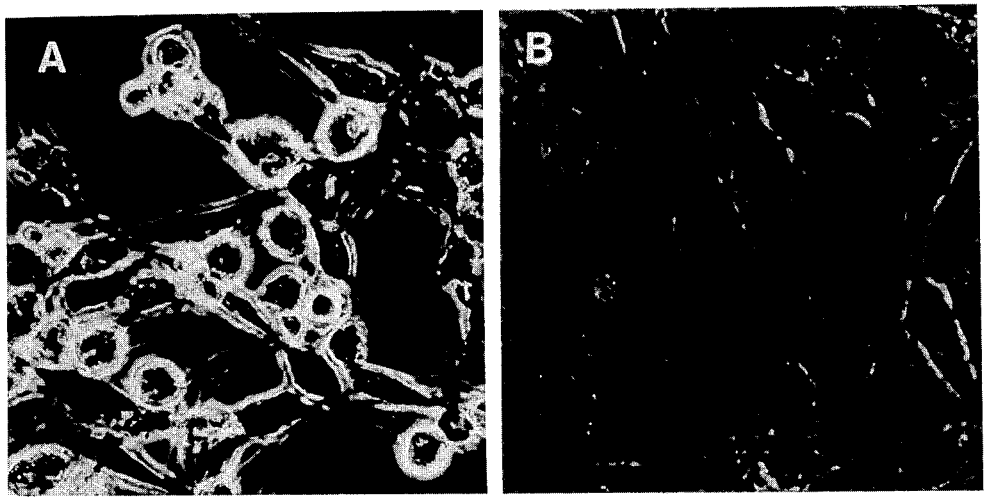
FIG. 5 shows two phase contrast micrographs (A & B) demonstrating morphology of SM-FRE cells grown in the absence (A) or presence (B) of CA, as described in Example 5.

SM-FRE cells were plated on glass coverslips and grown for three days in either the absence or the presence of 0.13 mM CA or 2 mM MdN. Phase contrast photographs were taken of the cells after fixation in 4% formaldehyde. SM-FRE cells grown in the presence of either CA (FIG. 5B) or MdN (not shown) for at least 48 hours exhibited a more flattened morphology in contrast to the more rounded morphology exhibited by untreated control cells (FIG. 5A). Treatment of SM-FRE cells with SW had no effect (not shown). If cells were plated at low density in the presence of CA, they grew only to a monolayer. At high density, cells that did not have room to attach and spread would die in the presence of CA. Twenty-four hours was sufficient to block cell surface expression of the v-fms transforming proteins; however, cells still appeared transformed at that time (see results in FIGS. 2C and 2D). Morphological reversion to the normal phenotype occurred only after at least two days' exposure to the drug. Because gp140$^{fms}$ disappears from the cell surface at least 24 hours before reversion to the normal morphology, some slower cellular events may be required for this process. Removal of the drug from the culture medium resulted in morphological retransformation (data not shown) indicating that the continuous presence of CA is required to maintain the normal morpholgy. This also suggests that the morphological change is not due to an induced differentiation of SM-FRE cells caused by CA.

Besides morphology, other features of the CA-treated SM-FRE cells indicated they had reverted to the normal phenotype. The media from SM-FRE cells grown in either CA or MdN was consistently less acidic than that from controls, indicating lower glucose consumption concomitant with decreased lactic acid production. Also, fibronectin was again expressed in the extracellular matrix of the treated cells, and bundles of microfilaments could be seen (data not shown). These properties are consistent with the re-expression of the normal phenotype in CA-treated SM-FRE cells.

EXAMPLE 6

Processing of v-fms proteins

Figure 6:
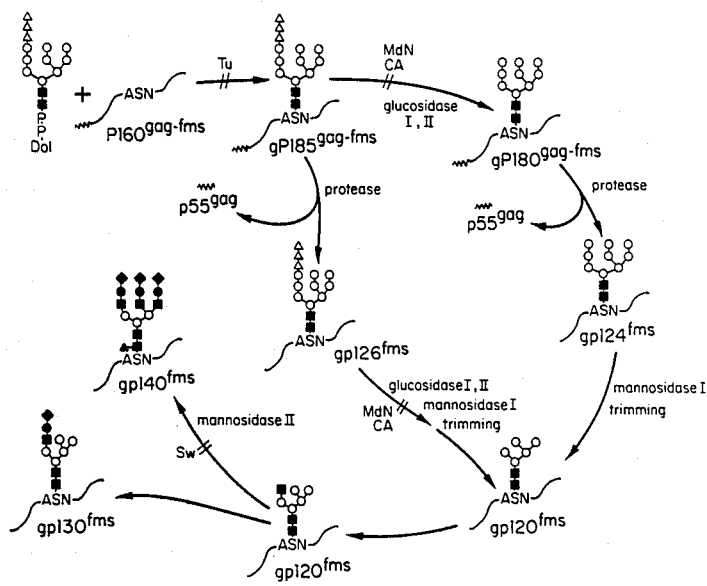
FIG. 6 is a diagrammatic representation of the glycosylational processing pathways for the v-fms gene products, as described in Example 6.

FIG. 6 summarizes the glycosylational processing sequence for the v-fms gene products and indicates the point at which each inhibitor acts. The molecular weights of the protein products are based on actual species that we detected either in the absence or presence of inhibitors, and on the known mechanism of action of these inhibitors. Only a short segment of the amino acid sequence surrounding a single asparagine (ASN) carbohydrate addition site is shown for the fms proteins. Eleven such sites exist in the extracellular domain of the fms protein. P.N.A.S. (USA) 81: 85-89, 1984. The name and molecular weight of each fms species is given according to standard nomenclature (*J. Virol.* 40: 953-957, 1981), and the specific points at which the inhibitors act are indicated. The normal processing pathway follows the circumference of the scheme and leads to gp140$^{fms}$.

The initial glycosylated product, gP185$^{gag\text{-}fms}$, is generated in the lumen of the endoplasmic reticulum (ER) by en bloc transfer of a Glc$_3$Man$_9$GlcNAc$_2$ oligosaccharide from a dolichol phosphate lipid carrier to asparagine residues of P160$^{gag\text{-}fms}$ undergoing synthesis on membrane-bound ribosomes. The nucleoside antibiotic TU, which inhibits the formation of Dol-P-P-N-acetylglucosamine, prevents glycosylation of P160$^{gag\text{-}fms}$. The newly-transferred Glc$_3$Man$_9$GlcNAc$_2$ oligosaccharide then undergoes a series of processing reactions during its transport through the ER and Golgi complex. Cleavage of the outer glucose residues by glucosidases I and II gives rise to gP180$^{gag\text{-}fms}$. Inhibition of glucosidase I by either CA or MdN prevents the formation of gP180$^{gag\text{-}fms}$ resulting in an accumulation of gP185$^{gag\text{-}fms}$, which is proteolytically cleaved to yield a non-glycosylated p55$^{gag}$ protein and a glycosylated gp126$^{fms}$ that is not expressed on the cell surface. Removal of the glucose residues and α1-2 linked mannose residues by both glucosidases I and II and mannosidase I generates gp120$^{fms}$ containing the Man$_5$GlcNAc$_2$ oligosaccharide. Addition of glcNAc to the α1-3 branch mannose (of the trimannosyl core) present on gp120$^{fms}$ allows the removal of both the α1-6 and α1-3 branching mannose residues by Golgi-mannosidase II. Further addition of glcNAc, gal, fuc, and/or sialic acid results in the complex type carbohydrate structure(s) appearing on the mature glycoprotein (gp140$^{fms}$). If SW is present, mannosidase II is inhibited and the gp120$^{fms}$ is shunted along a pathway leading to the synthesis of hybrid-type, gp130$^{fms}$ oligosaccharides. Of all the processing intermediates, only the gp140$^{fms}$ and gp130$^{fms}$ are expressed on the cell surface.

Discussion

The results presented in Examples 1 to 6 indicate that both proper carbohydrate processing and cell surface expression of the v-fms gene product are necessary for maintaining the transformed phenotype of SM-FeSV infected cells. Glycosylational processing inhibitors that block carbohydrate remodeling at an early stage (i.e., CA and MdN) within the rough ER prevent further processing, and the v-fms proteins do not reach the cell surface. These proteins presumably accumulate in the ER and still retain an associated tyrosine kinase activity that protrudes into the cytoplasm from the ER membrane. The cells, however, appear morphologically normal and do not grow well in soft agar. CA-treated cells also re-express fibronectin in the extracellular matrix and reform stress fibers (data not shown). In contrast, even when an abnormal processing intermediate of v-fms (i.e., the gp130$^{fms}$ species produced in the presence of SW) is expressed at the cell surface, the transformed state is maintained. By analogy with other onc proteins (*Mol. Cell. Biol.* 4: 1834-1842, 1985; *EMBO J.* 4: 105-112, 1985), it would seem likely that not only a functional transforming protein but also its transport to the appropiate subcellular target is necessary for transformation. Presumably the targets for the v-fms protein reside in the plasma membrane, but could be situated at some point in the endocytotic pathway as well.

Two other reports also have suggested that the cell surface expression of the v-fms proteins is necessary for transformation. *Cell* 40: 971-981, 1985; *Mol. Cell. Biol.* 4: 1999-2009, 1984. In these cases, deletions in the primary amino acid sequence were generated, and these deletions affected both the intracellular precursors and the final gp140$^{fms}$ product. One mutant lacked an associated kinase activity altogether. Thus, it was not possible to distingush between transforming functions of the precursors and those of the cell surface expressed gp140$^{fms}$. The glycosylational processing inhibitors, on the other hand, do not affect the primary amino acid sequence or the associated tyrosine kinase activity of the v-fms gene products. The mechanism of action of these inhibitors indicates that only carbohydrate processing is blocked within the transformed cells. This blockage at a step prior to surface expression was able to prevent anchorage independent growth and to revert cells to the normal phenotype.

The drugs that were effective at preventing transformation by SM-FeSV (i.e., CA and MdN) are not toxic to normal cells and did not reverse transformation by a retrovirus carrying a different oncogene (see Example 4). No overt toxicity was observed either in vitro (personal observations), or in short term (3-7 days) tests with CA in vivo (P.N.A.S. (USA) 82: 93-97, 1985). Also, similar drugs were without effect on normal erythroid differentation. *EMBO J.* 4: 105-112, 1985. It is surprising that such extracellular matrix glycoproteins as fibronectin can still function in CA-treated cells. N-linked carbohydrate on fibronectin, however, does not appear to play a role in either fibronectin secretion or in its ability to promote cell attachment and spreading. *J. Biol. Chem.* 258: 11883-11889, 1983; P.N.A.S. (USA) 76: 3343-3347, 1979. Therefore, fibronectin may still function in the observed reversion and spreading of the SM-FRE cells grown in the presence of CA.

Both drugs that were effective at preventing cell surface expression of gp140$^{fms}$ and reversing the transformed state blocked carbohydrate processing at the same early step. CA and MdN inhibit a glucosidase I and prevent trimming of the outermost glucose on the initial carbohydrate structure added to asparagine residues on the polypeptide backbone of the v-fms protein. gP185$^{fms}$ and the proteolytically processed products gp124$^{fms}$ and p55$^{gag}$ accumulate in the ER compartment. Presumably, a certain carbohydrate structure past this step is required for ticketing to the next compartment (the Golgi). Endocytotic uptake and intracellular targeting of lysosomal enzymes have been shown to depend on recognition of phosphomannosyl residues present on these glycoproteins. P.N.A.S. (USA) 74: 2026–2030, 1977; *J.Biol.Chem.* 255: 9608–9615, 1980. It has been proposed that some ER lectins may recognize specific carbohydrate structures and direct attached glycoproteins along proper pathways. *J. Biol. Chem.* 257: 14011–14017, 1982; *J. Cell. Biol* 98: 1720–1728, 1984. Such a model would be consistent with the lack of further transport and accumulation of gP185$^{gag\text{-}fms}$.

This is an attractive model and, as far as we could determine, the carbohydrate did not have any appreciable effect on any function or activity of the v-fms proteins other than limiting cell surface expression. All the precursors, whether abnormally process or not, still became phosphorylated in the in vitro kinase assay. Surprisingly, endocytosis of the v-fms proteins also was not affected by either SW, CA, or MdN. SW-treated SM-FRE cells were near normal in their endocytosis of v-fms proteins, and in the CA- or MdN-treated cells endocytosis still occurred even though very little v-fms protein found its way to the cell surface. These data suggest that carbohydrate structures affected by SW, CA, or MdN are probably not involved as determinants that specify accumulation in coated pits and subsequent endocytosis.

Glycosylational processing inhibitors similar (but not identical) to those used in the present studies were without dramatic effect on erbB transformed cells. *EMBO J.* 4: 105–112, 1985. Carbohydrate processing was abnormal yet the erB glycoprotein product was still expressed on the cell surface, and the cells remained transformed. This lack of effect may be due either to qualitative or quantitative differences in carbohydrate on erbB vs. fms proteins, but also could result from the use of less potent inhibitors. We are presently re-examining the sensitivity of erbB transformation to CA or MdN.

Recently the protein product of the c-fms proto-oncogene has been identified in both cats (*Science* 228: 320–322, 1985) and humans (see below). This product is a glycoprotein expressed on the surface of cells in the monocyte/macrophage lineage. It is not known yet whether activation and/or abnormal expression of this particular proto-oncogene is involved in any types of human tumors; however, there are indications that this may be the case. *J. Virol.* 48: 770–773, 1983. If so, glycosylational processing inhibitors, particularly CA and MdN, should be useful as anti-cancer drugs for these tumors. In addition, other transforming oncogenes whose transformation is mediated through glycosylated products, especially those that are ultimately expressed on the plasma membrane, may prove susceptible to chemotherapy with these inhibitors. Prevention of cell surface expression of oncogene products may be an effective means of regulating the transformed state.

SECOND SERIES OF EXAMPLES

To determine more about the mechanism of transformation by SM-FeSV, and especially about the comparative functions of the v-fms and c-fms proteins, we searched for and characterized the protein product of the human c-fms proto-oncogene. (Materials and methods are appended.)

EXAMPLE 7

BeWo cells express high levels of the c-fms message

In order to identify the protein product of the c-fms gene we first needed a cell line which expressed high levels of this protein. Previously published work has shown that several human neoplasms express relatively high levels of the c-fms mRNA. These included chronic myelogenous leukemias, Hodgkin's lumphomas, and mammary carcinomas from fresh human tumors. *Science* 224: 256–262, 1984. One human choriocarcinoma cell line, BeWo, has also been found to express relatively high levels of the c-fms mRNA. *J. Biol. Chem.* 258: 11219–11228, 1983. Based on this information, BeWo and several other cell lines were screened for expression of the c-fms mRNA.

TABLE 1 details the cell lines initially assayed for c-fms message. These cells were grown in culture, and total RNA was isolated from each. Serial dilutions of these RNAs were applied to nitrocellulose using a dot-blot manifold and probed with a nick-translated v-fms DNA. The probe was a 1.3 kilobase PstI-PstI fragment covering the kinase domain of the v-fms gene. *J. Virol.* 41: 489–500, 1982. This fragment has previously been shown to crosshybridize to the c-fms message. *Science* 224: 256–262, 1984.

TABLE 1

| Cell Lines Initially Screened for fms mRNA Expression | | |
|---|---|---|
| Cell Name | Cell Type | mRNA Expression$^a$ |
| BeWo | human choriocarcinoma | + |
| HL-60 | human promyelocytic leukemia | — |
| Colo-320DM | human colon adenocarcinoma | — |
| Nalm-1 | human pre-B leukemia | +/— |
| U-937 | human monocyte-like cell line | — |
| K-562 | human erythroid precursor (from CML patient) | — |
| MCF-7 | human breast carcinoma | — |
| RPMI6666 | human lymphoblasts, Hodgkins disease | — |
| IM-9 | human lymphoblast (from CML patient) | — |
| Mink | mink lung cells | — |
| SM-Mink | SM-FeSV infected mink lung cells | ++++ |

$^a$Amounts of fms hybridizing RNA were quantitated visually from an overnight exposure (preflashed film) of the dot blot. (—) indicates no hybridization was seen in the overnight exposure for 6 μg RNA. (+/—) indicates 10–50% of the hybridization seen for BeWo. The positive hybridizing RNAs were compared to the SM-mink dot and relative amounts are reflected in the number of +s.

Despite our attempts to find other cell lines which expressed high levels of the c-fms message, only BeWo cells had c-fms mRNA levels above background. BeWo cells were therefore considered the most likely to express detectable levels of the c-fms protein and were used for the following experiments.

EXAMPLE 8

A 140kd protein in BeWo cells is antigenically related to the v-fms proteins

Figure 7:
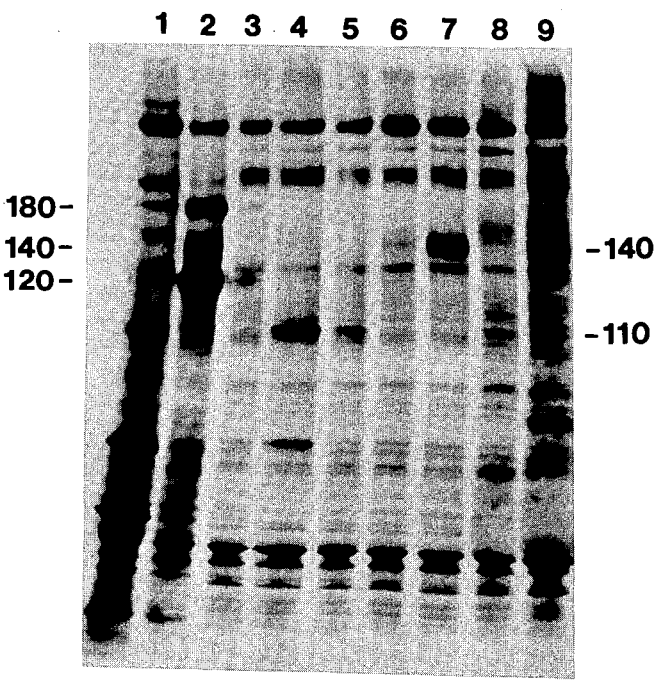
FIG. 7 shows nine electrophoresis gels (1-9) demonstrating that a cellular protein (BCP140) in BeWo cells is immunologically related to the viral fms proteins, as described in Example 8.

BeWo cells (FIG. 7, lanes 3–9) were labeled with [$^{35}$S]methionine for four hours, and detergent lysates were prepared. To look for a cross-reacting cellular protein, these lysates were screened with various antisera that reacted with the v-fms proteins. All the immune sera used were obtained from rats bearing SM-FRE tumors (TBR serum) and were known to precipitate the v-fms proteins. Of 35 antisera used, four precipitated proteins not recognized by normal sera. These four sera fell into two distinct classes: two (sera #21 and #40)

precipitated a protein of apparent molecular weight 110K (FIG. 7, lanes 4 and 5), and two (sera #26 and #27) precipitated a protein of apparent molecular weight 140K (FIG. 7, lanes 6 and 7).

Sera #21 and #40 also recognized a 110K protein in control lysates prepared from normal mink cells (FIG. 7, lane 1) and SM-FeSV transformed mink cells (FIG. 7, lane 2). As these cells were shown to express little or no c-fms mRNA it seemed unlikely that the 110K protein was the product of the c-fms gene.

Still referring to FIG. 7, lane 3 is normal rat serum, lane 8 is preimmune serum from rabbit #3667, and lane 9 is immune serum from rabbit #3667 directed against the trpE-vfms protein.

The sera used above were prepared by injecting SM-FeSV transformed FRE cells into (Wistar/Furth X Fischer) F1 rats (*Cell* 39: 327–337, 1984 and therefore might also recognize unrelated cellular proteins. To eliminate this possibility, antibodies were prepared to a segment of the v-fms protein expressed in bacteria. The 1.3 kilobase PstI-PstI v-fms DNA fragment encompassing almost the entire kinase-related domain at the 3' end of v-fms was cloned into a trpE expression vector, and antibodies were prepared in rabbits to this trpE-vfms fusion protein. Since these antisera are directed against a purified protein they are not likely to cross-react with unrelated cellular proteins. Serum from a rabbit immunized with this protein (but not preimmune sera from the same animal) recognized the 140K protein (FIG. 7, lanes 8 and 9).

When MCF-7 cells (which were negative for expression of c-fms mRNA) were screened with the above sera the 140K protein was not detected. Serum 190 21 precipitated the 110K protein in these cells, supporting the idea that the 110K protein is not related to the c-fms gene product (data not shown).

The level of the 140K protein in BeWo cells was considerably lower than the relative amount of gp140$^{v\text{-}fms}$ detected in SM-FeSV transformed cells. Based on the four-hour labeling with [$^{35}$S] methionine, scanning densitometry of immune precipitation results indicated that the 140K BeWo protein represented approximately 2% of all three v-fms proteins, or about 10–15% of the cell surface expressed gp140$^{fms}$. Actual steady state levels of these proteins are subject to potential differences in synthetic and turnover rates, but the values we obtained probably represent a close approxiamtion of these levels.

Because BeWo is a transformed cell line, the usual convention of naming cellular proteins as normal cell protein (NCP) was not applicable. Therefore, we chose to call the 140K protein BCP140 denoting a BeWo cell protein of 140K.

EXAMPLE 9

BCP140 is a glycoprotein

All three v-fms proteins are glycoproteins. *J. Virol.* 44: 696–702, 1982; *J. Virol.* 51: 730–771, 1984; *Cell* 39: 327–337, 1984; *Cell* 40: 971–981, 1985. As we have demonstrated above, this modification is important in the cell surface localization and function of these proteins. If BCP140 is the cellular homolog of the v-fms proteins then it might be expected to be a glycoprotein as well. To examine this possibility BeWo cells were labeled with [$^{3}$H]glucosamine and immunoprecipitated with normal and BCP140 cross-reacting sera. Both normal and SM-FeSV transformed mink cells were labeled and precipitated with anti-fms serum to serve as controls.

Lysates were prepared from [$^{3}$H]glucosamine-labeled (18 hrs.) mink (FIG. 8, lane 1), SM-mink (lane 2), and BeWo (lanes 3–6) cells and immunoprecipitated with the indicated sera: (lanes 1, 2, and 4) TBR serum #21; (lane 3) normal rat serum; (lane 5) TBR serum #26; and (lane 6) TBR serum #27.

Figure 8:
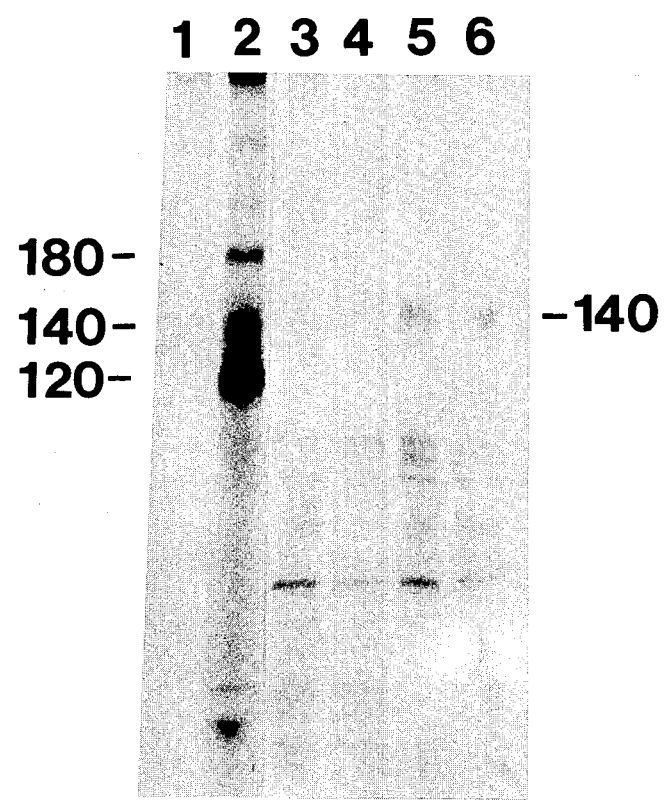
FIG. 8 shows six electrophoresis gels (1-6) demonstrating that BCP140 is a glycoprotein, as described in Example 9.

As can be seen in FIG. 8, three bands corresponding to the v-fms proteins were labeled with [$^{3}$H] glucosamine in transformed mink cells (lane 2), while normal cell controls (lane 1) were negative. BCP140 cross-reacting sera, but no control serum, immunoprecipitated a 140K protein (lanes 3, 5, and 6). BCP140 therefore appears to be a glycoprotein. The 110K band that is recognized by serum #21 was not labeled with [$^{3}$H] glucosamine (lane 4).

EXAMPLE 10

BCP140 is phosphorylated on tyrosine in an in vitro kinase assay

The nucleic acid sequence of v-fms reveals homology to the tyrosine kinase region of src and fes. P.N.A.S. (USA) 81: 85–89, 1984. Consistent with this information, all three fms proteins are labeled on tyrosine in an in vitro kinase assay. *J. Virol.* 40: 812–821, 1981. The cellular homolog of the v-fms proteins might be expected to behave similarly. To test this hypothesis, unlabeled lysates prepared from BeWo cells were immunoprecipitated with normal and BCP140 cross-reacting sera, and the immunocomplexes were assayed for kinase activity. In vitro labeled proteins were analyzed by gel electrophoresis.

Lysates were prepared from unlabeled SM-mink (FIG. 9A, lane 1) and BeWo (9A, lanes 2–6) cells and immunoprecipitated with the indicated sera: (lanes 1 and 4) TBR rat serum #21; (lane 2) normal rat serum; (lane 3) TBR serum #40; (lane 5) TBR serum #27; and (lane 6) TBR serum #26. Immunocomplexes were subjected to an in vitro kinase assay as detailed in Materials and Methods, and the labeled proteins were analyzed by SDS-PAGE.

Figure 9:
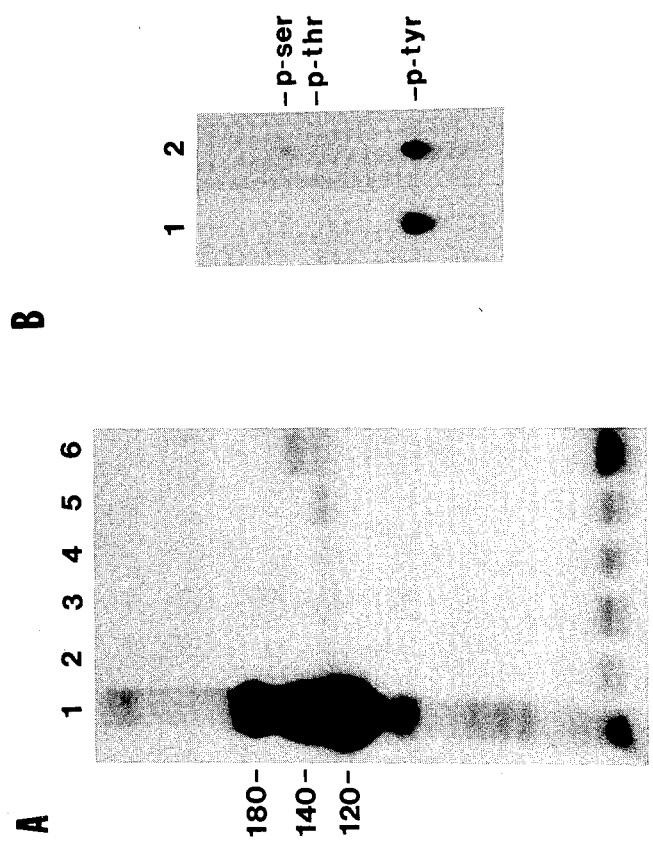
FIG. 9 shows two series of electrophoresis gels (A, 1-6, & B, 1-2) demonstrating that BCP140 has an associated in vitro tyrosine specific kinase activity, as described in Example 10.

The results from these experiments are shown in FIG. 9A. Under these conditions, the three v-fms derived bands were labeled efficiently (lane 1). A 140K band corresponding to BCP140 was labeled when BCP140 cross-reacting serum was used (lanes 5 and 6), but not with normal serum (lane 2). The 110K protein recognized by serum #21 and #40 was not labeled in this assay (lanes 3 and 4).

The requirements for divalent cations in these reactions were examined in kinase assays carried out under various conditions for both BCP140 and v-fms proteins. Requirements were identical for both. The kinase reaction would not occur in the presence of either EDTA or Ca++. Either Mn++ or Mg++ would allow the reaction to take place, but Mn++ was strongly preferred (data not shown).

To further characterize the kinase activity associated with BCP140, phosphoamino acid analysis was performed. Bands corresponding to gp120$^{fms}$ (FIG. 9B, lane 1) and BCP140 (9B, lane 2) were excised from the gel, and the eluted proteins were hydrolysed with 6M HCl at 110° C. Hydrolysates were analyzed by one-dimensional thin layer electrophoresis. The phosphoamino acids were resolved by one-dimensional high voltage electrophoresis at pH 3.5 and labeled spots were identified by their comigration with unlabeled standards.

In agreement with previously published work (J. Virol. 40: 812–821, 1981), the v-fms protein was labeled only on tyrosine (FIG. 9B, lane 1). BCP140 was labeled mainly on tyrosine, but trace amounts of serine were detected as well (FIG. 9B, lane 2). The phosphoserine detected in BCP140 may be due to background contamination with an adjacent phosphorylated band.

EXAMPLE 11

BCP140 is phosphoprotein in vivo

Despite its homology with other tyrosine kinases and its associated in vivo kinase activity, the v-fms proteins so far have not been found to contain phosphotyrosine in vivo. J. Virol. 40: 812–821, 1981; J. Virol. 38: 1084–1089, 1981. To examine the state of phosphorylation of BCP140 in vivo, cells were labeled for four hours with $^{32}$Pi. Detergent lysates were prepared from labeled cells, immunoprecipitated with normal and BCP140 cross-reacting sera, and analyzed by gel electrophoresis. Lysates were prepared from $^{32}$Pi-labeled (4hrs.) mink (FIG. 10A, lane 1), SM-mink (10A, lane 2), and BeWo (10A, lanes 3–7) cells and immunoprecipitated with the indicated antisera: (lanes 1, 2, and 5) TBR serum #21; (lane 3) normal rat serum; (lane 4) TBR serum #26; (lane 6) preimmune serum from rabbit #3667; and (lane 7) immune serum directed against the trpE-vfms fusion protein from rabbit #3667.

Figure 10:
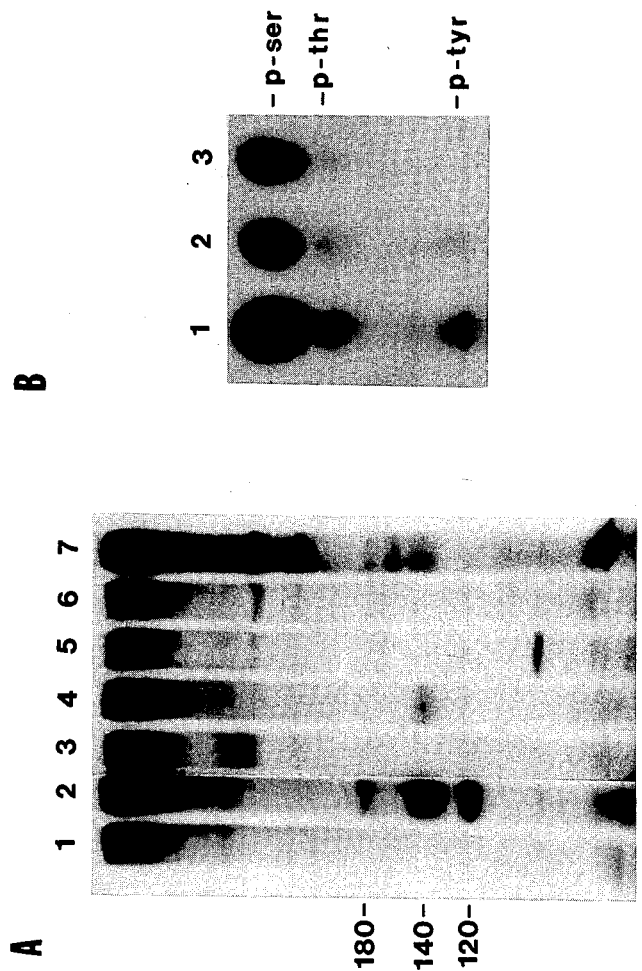
FIG. 10 shows two series of electrophoresis gels (A, 1-7, & B, 1-3) demonstrating that BCP140 is a phosphoprotein in vivo, as described in Example 11.

As can be seen in FIG. 10A, bands corresponding to the v-fms proteins were labeled in Sm-FeSV transformed, but not in normal mink lung cells (lanes 1 and 2). Similarly, BCP140 could be detected when lysates prepared from $^{32}$Pi-labeled BeWo cells were precipitated with immune sera (lanes 4 and 7), but not with control sera (lanes 3 and 6). Phosphorylated 110K protein was precipitated by serum #21 from BeWo cells (lane 5), but also from mink and SM-mink cells (lanes 1 and 2).

To further analyze the phosphoprotein nature of BCP140, phosphoamino acid analysis was performed on the in vivo labeled proteins. Bands corresponding to gp140$^{fms}$ (FIG. 10B, lane 1), gp120$^{fms}$ (10B, lane 2), and BCP140 (10B, lane 3) were excised from a gel and subjected to phosphoamino acid analysis. Phosphoamino acids were separated by high voltage electrophoresis and the labeled spots were identified by their comigration with unlabeled standards.

FIG. 10B shows that phosphoserine was the major phosphoamino acid present in each case. gp120$^{fms}$ and gp140$^{fms}$ both have trace amounts of phosphothreonine and phosphotyrosine. Trace amounts of phosphothreonine were detected in BCP140; however, very little or no phosphotyrosine could be seen even though as much phosphoserine was present in both BCP140 and gp120$^{fms}$. This difference in phosphotyrosine levels may be significant. Previous reports have not been able to detect phosphotyrosine in the v-fms proteins of metabolically $^{32}$Pi-labeled SM-FeSV transformed cells (J. Virol. 40: 812–821, 1981).

EXAMPLE 12

BCP140 is expressed on the cell surface

The product of the viral transforming gene (gp140$^{fms}$) is expressed on the cell surface where it may act as an analog of a growth factor receptor. J. Virol. 51: 730–771, 1984; Cell 39: 327–337, 1984. Cell surface expression of the v-fms protein is required for cell transformation. As demonstrated in the First Series of Examples above, when cell surface expression of the v-fms protein is blocked with glycosylation inhibitors the infected cells appear phenotypically normal. When cell surface expression is prevented by removal of the anchor sequence, the v-fms proteins will not cause cell transformation (Cell 40: 971–981, 1985). Since the surface localization of v-fms is so critical, we determined whether the c-fms protein also exhibited a cell surface localization.

Cell surface expression of BCP140 in subconfluent monolayers of BeWo cells was examined by labeling surface proteins by the chloramine T catalyzed protein iodination method described in J. Gen. Virol. 29: 127–131, 1975. Lysates from labeled cells were immunoprecipitated with normal and BCP140 cross-reacting sera and analyzed by gel electrophoresis.

Viable, subconfluent BeWo cells were labeled on their surface proteins by the chloramine-T catalyzed method of protein iodination. The reaction was terminated with the addition of -ME, lysates were prepared, and immunoprecipitated with the indicated antisera: (FIG. 11, lane 1) normal rat sera; (lane 2) TBR serum #26; (lane 3) preimmune serum from rabbit #3667; and (lane 4) immune serum directed against the trpE-vfms fusion protein from rabbit #3667.

Figure 11:
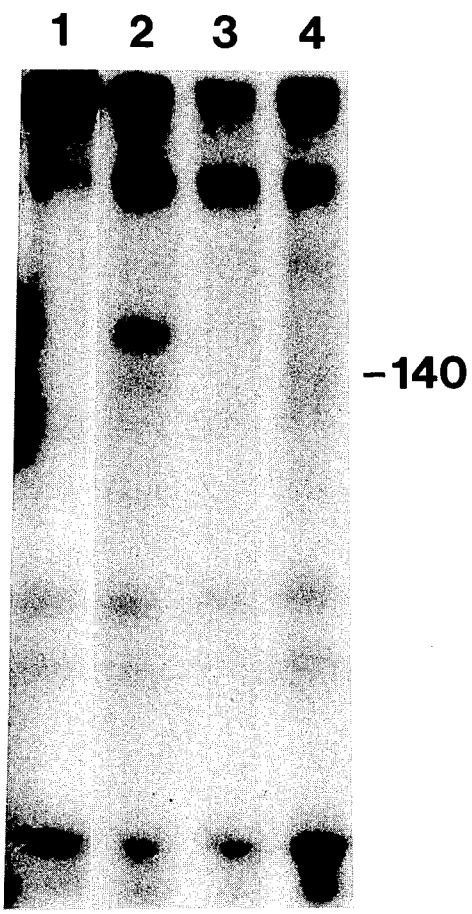
FIG. 11 shows four electrophoresis gels (1-4) demonstrating that BCP140 is expressed on the cell surface, as described in Example 12.

The results are shown in FIG. 11. A 140K was detected with BCP140 cross-reacting sera (lanes 2 and 4), but not with normal controls (lanes 1 and 3). A band of approximate molecular weight 170K was also precipitated (lane 2). A band of corresponding size is sometimes precipitated in methionine-labeled lysate. As this protein is not reproducibly precipitated its significance is doubtful. Because the c-fms proteins are present in very low levels, detection of cell surface expressed c-fms was expected to be difficult. The very low levels of the BCP140 band seen in FIG. 11 reflect this difficulty.

EXAMPLE 13

BCP140 is structurally related to gp120$^{fms}$.

The primary polypeptide structure of BCP140 and gp120$^{fms}$ were compared by two-dimensional tryptic fingerprint analysis. [$^{35}$S]methionine labeled bands were excised from gels, the proteins eluted and digested with TPCK trypsin. The tryptic peptides were separated on thin layer plates by electrophoresis in the horizontal dimension and chromatography in the vertical dimension.

[$^{35}$S] methionine labeled fms proteins were immunoprecipitated from lysates of BeWo and SM-mink cells, purified by SDS-PAGE, and digested with TPCK-trypsin. Tryptic peptides were resolved by high voltage electrophoresis in the horizontal dimension, and by chromatography in the vertical dimension. FIG. 12: (panel A) tryptic fingerprint of gp120$^{fms}$; (panel B) tryptic fingerprint of BCP140; (panel C) tryptic fingerprint of a mixture of peptides from BCP140 and gp120$^{fms}$. The pattern of tryptic peptides in panel C is represented by the diagram in panel 12D, where solid spots represents peptides common to both BCP140 and gp120$^{fms}$; open spots represent peptides present only in gp120$^{fms}$; and dotted spots represent peptides present only in BCP140.

FIG. 12 shows that the tryptic fingerprints of BCP140 and gp120$^{fms}$ are similar (panels A and B). When peptides from both proteins were mixed prior to separation, eight peptides were shown to have co-migrated (panel C). The results from this experiment are summarized schematically in panel D.

The amino acid sequence of the v-fms protein, as determined from nuleic acid sequence (P.N.A.S. (USA) 81: 85-89, 1984), predicts 16 methionine-containing tryptic peptides. However, several of these are very large and are not expected to appear in the tryptic fingerprints. Three of the predicted methionine-containing peptides have the carbohydrate addition consensus sequence, asn-X-ser(thr). Carbohydrate-containing peptides do not migrate during chromatography and remain unresolved at the bottom of the tryptic map. The presence of such an unresolved spot in the BCP140 map is additional evidence for the glycosylation of that protein.

EXAMPLE 14

TPA induces ML-1 cells contain a c-fms protein

In order to confirm that BCP140 was the c-fms gene product, we wanted to find other human cells expressing the c-fms protein. As a murine myelomonocytic leukemia was previously found to contain elevated c-fms RNA (*Nature* 310: 249-251, 1984), we tested human cells in the same lineage. The cells and their levels of c-fms RNA are presented in TABLE 2.

TABLE 2
Additional Cell Lines Screened for fms mRNA Expression.

| Cell Name | Cell Type | mRNA Expression[a] |
|---|---|---|
| Uninduced ML-1 | human myeloblastic leukemia | +/− |
| TPA induced ML-1 | human monocyte-like | +++ |
| DMSO induced ML-1 | human granulocyte-like | +/− |
| TPA induced HL-60 | human monocyte-like | +++ |
| DMSO induced HL-60 | human granulocyte-like | − |
| Adherent monocytes | normal human adherent monocytes | ++ |

[a]Amounts of fms hybridizing RNA were quantitated visually from an overnight exposure (preflashed film) of the dot blot. (−) indicates no hybridization was seen in the overnight exposure for 6 μg RNA. (+/−) indicates 10-50% of the hybridization seen for BeWo. The positive hybridizing RNAs were compared to the SM-mink dot and relative amounts are reflected in the number of +s.

ML-1 cells are a line of human myeloblastic leukemia cells that can be induced to differentiate into monocytes/macrophages with TPA or into granulocytes with DMSO. *Cancer Research* 42: 5152-5158, 1982. Cells were grown in culture and total RNA was isolated from uniduced, TPA induced, and DMSO induced cells. RNA dotblots were probed with v-fms DNA to determine the levels of c-fms mRNA present.

Total RNA was isolated from the indicated cell lines: (FIG. 13, lane 1) SM-FeSV infected mink; (lane 2) MCF-7; (lane 3) BeWo; (lane 4) uninduced ML-1; (lane 5) TPA induced ML-1; (lane 6) DMSO induced ML-1; and (lane 7) normal human adherent monocytes. SM-mink and MCF-7 RNAs were included to serve as positive and negative controls, respectively. Serial dilutions (6 μg, 2 μg, and 0.7 μg) were spotted on nitrocellulose. The blot was baked, prehybridized, and finally hybridized with a nick-translated PstI-PstI v-fms fragment covering almost the entire kinase domain.

Only very low levels could be detected in uninduced cells (FIG. 13, lane 4); however, when these cells were induced with TPA a large increase in c-fms specific message was seen (lane 5). DMSO induction caused no obserable increase in the level of c-fms RNA (lane 6). These results were verified by Northern analysis (not shown).

Figure 14:
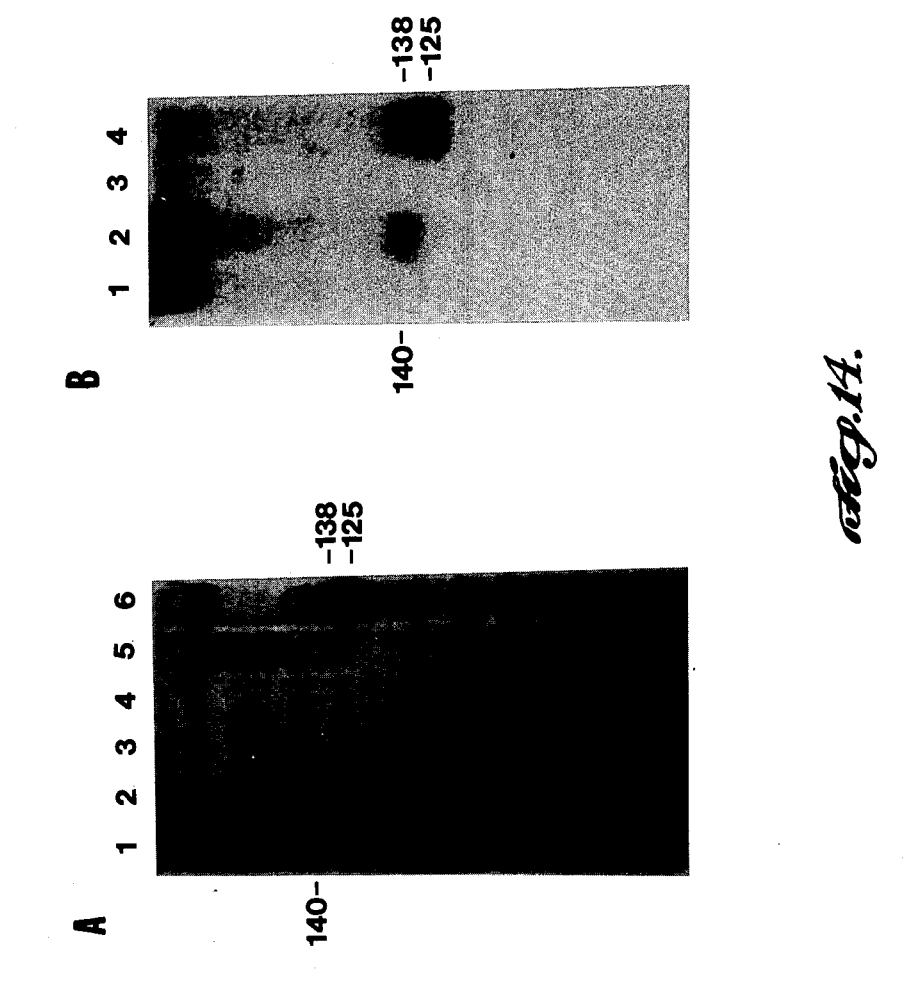

In order to see if expression of mRNA correlated with expression of a c-fms protein, ML-1 cells were labeled with [$^{35}$S] methionine and immunoprecipitated with normal and BCP140 cross-reacting sera. Lysates prepared from [$^{35}$S] methionine labeled (4 hrs.) BeWo (FIG. 14A, lanes 1 and 2), uninduced ML-1 (lanes 3 and 4), and TPA-treated ML-1 (lanes 5 and 6) cells, were immunoprecipitated with either normal (lanes 1, 3, and 5) or BCP140 cross-reacting serum (TBR serum #26; lanes 2, 4, and 6). The results were analyzed by SDS-PAGEe The results from these experiments are shown in FIG. 14A. A doublet specific for immune sera was seen in TPA-treated cells (lanes 5 and 6) but not in uninduced ML-1 cells (lanes 3 and 4). The upper band of this doublet was reproducibly smaller than the BCP140 and was assigned an apparent molecular weight of 138K. The lower band has an apparent molecular weight of 125K.

Kinase activity was examined by incubating immunocomplexes from both BeWo and TPA induced ML-1 lysates with [$^{32}$P] ATP and Mn++. Lysates prepared from unlabeled BeWo (FIG. 14B, lanes 1 and 2) and TPA-treated ML-1 (lanes 3 and 4) cells were immunoprecipitated with either normal serum (lanes 1 and 3) or BCP140 cross-reacting serum (TBR serum #26; lanes 2 and 4). Immunoprecipitates were subjected to an in vitro kinase assay and the results were analyzed by SDS-PAGE. After an initial exposure (not shown), the gel was incubated in 1M NaOH for 90 min. at 55° and washed for 90 min. in 10% acetic acid, 10% isopropanol. *Methods in Enz.* 99: 587-602, 1983. This procedure specifically removes phosphoserine, thus enhancing the gel for phosphotyrosine containing bands.

As FIG. 14B shows, bands corresponding to BCP140 (lanes 1 and 2) and the ML-1 doublet (lanes 3 and 4) were detected with immune but not with normal sera. This indicates that the ML-1 doublet, similarly to BCP140, behaves like a substrate for a tyrosine kinase in vitro.

EXAMPLE 15 c-fms is present in the human monocyte/macrophage lineage

Our results with ML-1 cells suggest that c-fms may be expressed in human monocyte/macrophage cells. To determine if this is the case we examined HL-60 cells, a human promyelocytic leukemia cell line. Like ML-1 cells, HL-60 cells can be induced to differentiate into monocytes with TPA (P.N.A.S. (USA) 76: 2779-2783, 1979) or into granulocytes with retinoic acid (P.N.A.S. (USA) 75: 2458-2462, 1978). When RNA from TPA induced and uninduced HL-60 cells was probed with c-fms a large (greater than 10-fold) increase in c-fms message was seen in TPA-treated cells. No increase was seen with induction by retinoic acid (data not shown).

Figure 13:
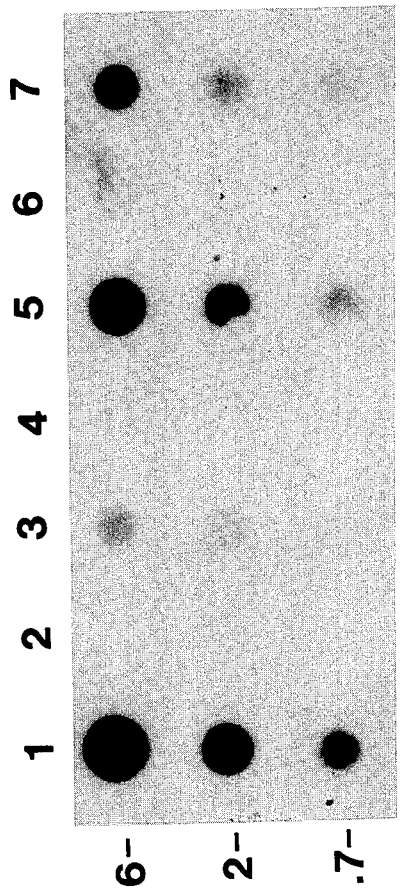
FIG. 13 shows serial dilutions (6, 2, .7) of total RNA isolated from seven cell lines (1-7) hybridized with a v-fms fragment, demonstrating the expression of c-fms mRNA in the macrophage lineage as described in Examples 14 and 15.

Finally, we examined normal human monocytes. Monocytes were isolated from blood and allowed to adhere to tissue culture plastic. Total RNA was prepared and applied to nitrocellulose using a dotblot manifold. When these dotblots were probed with nick-translated v-fms DNA, levels of c-fms RNA intermediate between those of BeWo cells and TPA induced ML-1 cells were observed (FIG. 13, lane 7). When immunocomplexes from monocytes were assayed in an in vitro kinase assay, a protein doublet was labeled which comigrated with that seen in ML-1 cells (data not shown).

EXAMPLE 16

Castanospermine-dependent inhibition of monocyte/granulocyte colony formation

Hemopoietic bone marrow cells were cultured with CA at concentrations ranging from 75 μg/ml to 200 μg/ml. Normal erythroid colonies formed in normal amounts. In contrast, formation of monocyte/granulocyte colonies was inhibited. The inhibition exhibited a titration effect that directly related with CA concentration, which indicated that the suppression of monocyte/granulocyte colony formation was drug-dependent.

Discussion.

The results presented in Examples 7 to 15 identify the human cellular homolog of the viral fms protein. This protein (BCP140) was first identified as a 140K glycoprotein in BeWo cell lysates capable of being immunoprecipitated with anti-sera directed against the viral fms protein (but not normal sera). In addition to being antigenically similar, BCP140 was shown to be structurally related to the viral fms proteins by tryptic finerprint analysis. BCP140 is a glycoprotein that is expressed on the cell surface. It possesses an in vitro associated tyrosine kinase activity; however, when labeled in vivo with $^{32}Pi$ the major phosphoamino acid detected was phosphoserine. In all of these respects BCP140 is similar to the viral fms proteins.

Additional evidence that BCP140 is the protein product of the c-fms gene is provided by immunoprecipitations of other cell lines. Proteins recognized by our c-fms cross-reacting sera could be specifically immunoprecipitated from human cells which expressed high levels of the c-fms mRNA (BeWo, TPA induced ML-1, and normal monocytes), but not from cells which did not express detectable levels of the c-fms message (uninfected mink, uninduced ML-1, and MCF-7).

The c-fms proteins detected in TPA treated ML-1 cells and normal monocytes differed from BCP140 in that they were a doublet of 125 K and 138K. The relationship between the doublet c-fms proteins seen in TPA induced ML-1 cells is similar to that seen between the two v-fms proteins, $gp120^{fms}$ and $gp140^{fms}$. Pulse-chase experiments in virally transformed cells show that a precursor product relationship exists between $gp120^{fms}$ and $gp140^{fms}$ proteins. *J. Virol.* 51: 730–771, 1984. Similarly, data from pulse-chase experiments performed with TPA induced ML-1 cells has shown that the lower band (125K) is a precursor of the upper band (138K) which has a half-life of less than 30 min. (our unpublished results). Unlike the viral fms product, essentially all of the precursor protein appears to be converted to the higher molecular weight species. The slightly greater molecular weight of the lower c-fms band (125K), as compared to the lower v-fms band (120K), may suggest a difference in the size of the viral and cellular proteins. Presumably, both these forms of fms proteins contain high mannose-type carbohydrate chains; however, species specific differences in glycosylation would make direct interpretation of relative molecular weight of the proteins difficult.

It is interesting that BeWo cells lack the lower molecular weight band found in ML-1 cells, normal monocytes, and the viral proteins. This could be due to much more efficient processing of the lower molecular weight precursor, or alternately to greater stability of the mature species in BeWo cells. This latter possibility is consistent with the protein levels seen in BeWo and ML-1 cells. While TPA-stimulated ML-1 cells have approximately 10-fold higher levels of c-fms mRNA than do BeWo cells, the levels of protein in these two cells is comparable (at most, the c-fms proteins in ML-1 are expressed at levels two- to three-fold higher than in BeWo cells). The higher molecular weight species in ML-1 cells has a very short half life (less than 30 minutes). If BCP140 had a very long half life (due perhaps to inefficient endocytosis), it would account for both the level of proteins seen in these cells and the accumulation of the higher molecular weight species. The difference in apparent molecular weights of the larger c-fms protein in ML-1 cells (138K) and that in BeWo cells (140K) is again most likely due to differences in glycosylation between the different cell types.

The presence of c-fms mRNA and protein in normal adherent monocytes and in ML-1 cells induced to differentiate into monocytes and macrophages with TPA suggest that c-fms functions in this pathway. This pathway originates with pluripotent stem cells in the bone marrow. These cells undergo commitment and differentiate sequentially through stages that are morphologically distinguishable. The later phases of this monocytic lineage include the production of monoblasts, promonocytes, circulating monocytes, adherent monocytes, and eventually macrophages. Metcalf, D., *The Hematopoietic Colony Stimulating Factors,* Elsevier Science Publishers, 1984; Stanley, E. R., Colony stimulating factors, in *The Lymphokines,* W. E. Steart II & J. W. Hadden, eds., Humana Press, pp 102–132, 1981. A number of factors are active in this lineage, including interleukin 3, GM-CSF and M-CSF. The major growth factor that drives proliferation and differentiation along this lineage exclusively, however, is M-CSF (also called CSF-1). *Cell* 28: 71–81, 1982. We contemplate that the c-fms proto-oncogene encodes the receptor for one or more of these growth factors. The c-fms proto-oncogene glycoproteins may also appear on the surface of myeloblastic lineage cells, such as granulocytes (neutrophils), as well.

It is interesting to note that the c-fms gene has been localized to the long arm of chromosome five (*Virol.* 126: 248–258, 1983; *J. Virol.* 48: 770–773, 1983), and that a specific deletion in the long arm of chromosome five may be correlated with a predisposition to myeloid leukemia in some patients (*Blood* 46: 519–533, 1975). It has been suggested that many human leukemias result from a block in the differentiation pathway of certain hematopoietic cell lineages. Consistent with this idea, when some myeloid leukemic cells are induced to differentiate with exogenous factors they are no longer cancerous in vivo (*J. Cell Physiol.* 86: 221, 1975; *Int. J. Cancer* 38: 375, 1981). From our work with monocytes it appears than c-fms is expressed as monocytes differentiate from precursor cells. We contemplate that alteration of the c-fms gene would drive proliferation of monocytic precursor cells resulting in abnormal hematopoietic maturation and neoplasia.

Another mechanism that could account for oncogenic potential of the c-fms gene involves activation and inappropriate tissue expression. Fibroblasts, as well as most embryonal tissues of the mouse, do not contain significant RNA for c-fms (*Mol. and Cell. Biol.* 3: 1062–1069, 1985; *Nature* 304: 484–486, 1983), yet fibroblasts, at least, are readily transformed by the product of the v-fms gene. It is interesting that the product of the c-fos gene also is expressed in the mononuclear phagocytic lineage (*Cell* 40: 209-217, 1985), and its inappropriate expression in other tissues has been proposed as a mechanism to explain its transforming activity (*Cell* 36: 51-60, 1984).

An additional suggestion as to the possible molecular mechanism of transformation by fms proteins stems from the different state of in vivo phosphorylation between the v-fms and c-fms gene products. In vivo, both the viral proteins and BCP140 are labeled strongly on serine with $^{32}$Pi. While the v-fms proteins exhibit trace amounts of phosphothreonine and phosphotyrosine, BCP140 has trace amounts of phosphothreonine only. This extremely low level of phosphotyrosine in the viral proteins and the observation that levels of total phosphotyrosine in infected cells are not detectably elevated has suggested that the viral proteins are not active as tyrosine kinases in vivo. Our results may indicate that the v-fms proteins have a very low level of phosphotyrosine, perhaps as a result of autophosphorylation. This is in good agreement with the model that v-fms is an altered receptor which is constitutively providing a proliferative signal to the host cell, due either to mutation or truncation of original c-fms regulatory sequences. Perhaps both modifications of the c-fms sequences and expression outside of the normal tissue may be necessary for transformation. In contrast, the c-fms protein remains inactive until the binding of an appropriate factor at which time its kinase would be activated resulting in controlled cell proliferation.

Materials and Methods

Cell Culture. Uninfected mink cells (CCL 64) and SM-FeSV infected mink cells (CL 15-1) were grown in Delbecco's Modified Eagle's Medium (DMEM) as described in *Cell* 39: 327-337, 1984. BeWo cells (CCL 98) (*Cancer Res.* 28: 1231-1236, 1968) was obtained from the American Type Culture Collection (Rockville, MD), and grown in Ham's F12 supplemented with 15% heat inactivated fetal bovine serum (HI-FBS). ML-1 cells (*Cancer Res.* 42: 5152-5158, 1982) were obtained from Alexander Bloch (Roswell Park Memorial Institute), and grown in RPMI supplemented with 10% HI-FBS. ML-1 cells were induced to differentiate into monocytes by incubation in culture medium supplemented with $5 \times 10^{-10}$M TPA (12-0-tetradecanoyl-phorbol-13-acetate) for two days. Granulocyte differentiation was induced by incubation in culture medium supplemented with 1.25% DMSO for two days as well. Normal human adherent monocytes were obtained from Dr. Richard M. Locksley (Veterans Administration Hospital, Seattle). Briefly, monocytes were prepared from 10 ml heparinzed venous blood and separated by centrifugation over Histopaque (Sigma Chemical Co.) (*Scand. J. Clin. Lab. Invest.* 21(Suppl. 97): 77-85, 1968). Mononuclear cells collected at the interface were selected by adherence to 75 cm$^2$ tissue culture flasks (*J. Clin. Invest.* 69: 1099-1111, 1982).

Antiserum. Rat antisera directed against viral fms proteins were prepared in rats as previously in *Cell* 39: 327-337, 1984. Briefly, the PstI-PstI fragment encoding the C-terminus of v-fms was cloned into the E. coli trp E bacterial expression vector pATH-11 (gift of T.J. Koerner, Columbia University), and the bacteria were induced to overproduce the v-fms-trpE fusion protein. Approximately 100 μg of partially purified fusion protein (*Science* 214: 1125-1129, 1981; *J. Virol.* 49: 132-141, 1984) in Freund's complete adjuvant was injected S.C. into rabbits and they were boosted every four weeks with 50-100 μg protein in Freund's incomplete adjuvant. Rabbits were bled after the second boost.

Rabiolabeling and immunoprecipitations. Cells labeled with [$^{35}$S]methionine were incubated in methionine-free DMEM supplemented with 5% HI-FBS and 100-200μ Ci/ml of radioactive methionine for four hours. Cells labeled with $^{32}$Pi were incubated in phosphate-free DMEM supplemented with 5% HI-FBS and 2.5 mCi/ml $^{32}$P-orthophosphate (carrier free, Neew England Nuclear) for four hours. Cells labeled with [$^3$H]glucosamine were incubated in glucose-free DMEM supplemented with 5% HI-FBS, 10 mM fructose, and 50μ Ci/ml glucosamine HCl, D-[1,6-$^3$H]-glucosamine HCl (39.9 Ci/mmole; New England Nuclear) for 18 hours. Cell surface proteins were labeled by the chloramine-T method of protein iodination (*J. Gen. Virol.* 29: 127-131, 1975) as described in *Cell* 39: 327-337, 1984. In all cases lysates were prepared from labeled cells and used for immunoprecipitations as previously reported except that a high salt buffer wash (2M NaCl; 10 mM Tris pH 7.2; 0.5% DOC; 1% NP-40) was included after the 1M MgCl$_2$ wash (*J. Biol. Chem.* 258: 11219-11228, 1983). In some cases lysates were "pre-cleared" by immunoprecipitation with normal rat serum.

Kinase Assays and Phosphoamino Acid Analysis. Immunoprecipitates from unlabeled cell lysates were collected on fixed *Staphylococcus aureus* and washed twice with RIPAE buffer; once with lysis buffer (10 mM Tris pH 7.2; 50 mM NaCl; 0.5% NP-40); and once with calcium and magnesium-free PBS. Washed immunocomplexes were incubated in 30 microliters kinase buffer (10 mM MnCl$_2$; 20 mM Tris pH 7.5) with 10μ CiY-$^{32}$P-ATP for 10 min. at 30°. The reaction was terminated with the addition of RIPAE buffer and washed once with 1M MgCl$_2$; 10 mM Tris pH 7.2; once with high salt buffer, and once with lysis buffer. The labeled proteins were resolved by SDS-PAGE. To determine the divalent cation requirements for the kinase reaction, either MgCl$_2$, CaCl$_2$, or EDTA was substituted of MnCl$_2$ in the above procedure. $^{32}$Pi labeled proteins were eluted from gel slices by the procedure of Beemon and Hunter (*J. Virol.* 28: 551-556, 1978), and phsphoamino acid analysis of the eluted proteins was preformed as detailed in *Methods in Enz.* 99: 587-602, 1983.

Two-Dimensional Tryptic Peptide Analysis. Two-dimensional tryptic fingerprints were prepared from [$^{35}$S]methionine-labeled proteins as described in *Virology* 62: 319-336, 1974. Tryptic peptides were resolved by high voltage electrophoresis in the horizontal dimension using an electrophoresis buffer of butanol:pyridine:acetic acid:water (2:1:1:36) for 90 min. at 1.1 kV, and by chromatography in the vertical dimension using butanol:pyridine:acetic acid:water (97:75:15:60) until the solvent front was 1-2 cm from the top of the plate. The plates were sprayed with Enhance (New England Nuclear) prior to exposure.

RNA Isolation and Blots. Total cellular RNA was isolated by the method described in *J. Mol. Biol.* 106: 403-420, 1976. RNA was denatured by incubation in 20×SSC: 37% formaldehyde (3:2) for 15 min. at 60°. Serial dilutions were applied to nitrocellulose (which had previously been soaked in 20×SSC and dried) using a dot blot manifold. The nitrocellulose was then dried and baked at 80° in vacuo for 90 min. Blots were prehybridized at 42° overnight in a solution containing 50% formamide, 5×SCC, 10 mM sodium phosphate (pH 6.5), 300μ g/ml sheared salmon sperm DNA, 1×Denhardt's solution. They were then hybridized at 42° in the same solution with the addition of 10% dextran sulfate and 1×10⁶ cpm/ml nick-translated PstI v-fms probe for 8-24 hours. Blots were washed twice in 2 SSC; 0.1% SDS at room temperature, and twice in 0.1×SSC; 0.1% SDS at 55°.

While the present invention has been described in conjunction with a preferred embodiment and illustrative examples, one of ordinary skill after reading the foregoing specification will be able to effect various changes, substitutions of equivalents, and other alterations to the methods set forth herein. It is therefore intended that the protection granted by Letters Patent hereon be limited only by the definition contained in the appended claims and equivalents thereof.

The embodiments of the invention in which an exclusive property or privilege is claimed are defined as follows:

1. A method of regulating oncogene-medicated cell transformation in a host, comprising the step of administering to a host comprising cells tranformed by an oncogene having a glycosylated expression product an amount of processing glucosidase inhibitor effective to revert the transformed cells to a normal phenotype.

2. The method of claim 1 wherein said processing glucosidase inhibitor is selected from the group consisting of castanospermine, N-methyl-1-deoxynojirimycin, 1-deoxynojirimycin, 5-amino-5-deoxy-D-glucopyranose, and bromoconduritol.

3. The method of claim 1 wherein said processing glucosidase inhibitor inhibits glucosidase I.

4. The method of claim 3 wherein said glucosidase I inhibitor is selected from the group consisting of castanospermine, N-methyl-1-deoxynojirimycin, 1-deoxynojirimycin, and 5-amino-5-deoxy-D-glucopyranose.

5. The method of claim 4 wherein said glucosidase I inhibitor is selected from the group consisting of castanospermine and N-methyl-1-deoxynojirimycin.

6. The method of claim 5 wherein said glucosidase I inhibitor is castanospermine.

7. The method of claim 1 wherein said glycosylated expression product is expressed on the plasma membrane of a transformed cell.

8. The method of claim 7 wherein said glycosylated expression product is a growth factor receptor.

9. The method of claim 1 wherein said glycosylated expression product is released from a transformed cell.

10. The method of claim 9 wherein said glycosylated expression product is a growth factor.

11. The method of claim 1 wherein said oncogene is selected from the group consisting of fms, erbB, sis, and neu oncogenes.

12. A method of determining whether an oncogene is susceptible to regulation by a processing glucosidase inhibitor, comprising the steps:
contacting cells transformed by an oncogene having a glycosylated expression product with a processing glucosidase inhibitor, and
determining that the oncogene is susceptible to regulation by the processing glucosidase inhibitor if the transformed cells revert to a normal phenotype in the presece of the processing glucosidase inhibitor.

13. The method of claim 12, wherein reversion to a normal phenotype comprises reversion of anchorage independence of growth.

* * * * *

UNITED STATES PATENT AND TRADEMARK OFFICE
CERTIFICATE OF CORRECTION

PATENT NO. : 4,837,237  
DATED : June 6, 1989  
INVENTOR(S) : Rohrschneider et al.

Page 1 of 2

It is certified that error appears in the above-identified patent and that said Letters Patent is hereby corrected as shown below:

Column 2, line 9:  "acknowledge" should be --acknowledged--

Column 2, line 40:  "differentation" should be --differentiation--

Column 3, line 39:  "descibed" should be --described--

Column 4, line 33:  "dolicho" should be --dolichol--

Column 4, lines 50-51:  "repsec-tive" should be --respective--

Column 6, line 54:  "mocroscopy" should be --microscopy--

Column 6, lines 65-66:  "perozi-dase" should be --peroxidase--

Column 7, line 62:  "The" should be --the--

Column 8, line 60:  "morpholgy" should be --morphology--

Column 9, line 27:  "en bloc" should be --en bloc--

Column 10, line 28:  "distingush" should be --distinguish--

Column 10, line 48:  "differentation" should be --differentiation--

Column 10, line 65:  "gP185$^{fms}$" should be --gP185$^{gag\text{-}fms}$--

Column 11, line 17:  "process" should be --processed--

Column 11, line 34:  "erB" should be --erbB--

Column 12, line 9:  "lumphomas" should be --lymphomas--

Column 13, line 34:  after "Serum" delete "190" and insert --   -- (space)

Column 13, line 48:  "approxiamtion" should be --approximation--

Column 14, line 13:  "no" should be --not--

UNITED STATES PATENT AND TRADEMARK OFFICE
CERTIFICATE OF CORRECTION

PATENT NO. : 4,837,237
DATED : June 6, 1989
INVENTOR(S) : Rohrschneider et al.

It is certified that error appears in the above-identified patent and that said Letters Patent is hereby corrected as shown below:

Column 15, line 12: after "is" insert --a--
Column 16, line 27: after "140K" insert --band--
Column 16, line 32: "lysate" should be --lysates--
Column 17, line 66: "obserable" should be --observable--
Column 18, line 11: "PAGEe" should be --PAGE.--
Column 19, line 41: "125 K" should be --125K--
Column 21, line 52: "heparinzed" should be --heparinized--
Column 22, line 9: "Neew" should be --New--
Column 22, line 44: "phsphoamino" should be --phosphoamino--
Column 22, line 66: "in vacuo" should be --$\underline{in}$ $\underline{vacuo}$--
Claim 1, line 20: "medicated" should be --mediated--
Claim 11, lines 2-3: "fms, erbB, sis, and neu" should be --$\underline{fms}$, $\underline{erb}$B, $\underline{sis}$, and $\underline{neu}$--
Claim 12, line 10: "presece" should be --presence--

Signed and Sealed this

Sixth Day of November, 1990

Attest:

HARRY F. MANBECK, JR.

Attesting Officer  Commissioner of Patents and Trademarks